United States Patent
Gong et al.

(10) Patent No.: US 10,487,044 B2
(45) Date of Patent: Nov. 26, 2019

(54) GAMMA-AMINOBUTYRIC ACID HEMIHYDRATE CRYSTAL AND PREPARATION METHOD THEREOF

(71) Applicants: NANTONG LICHENG BIOLOGICAL ENGINEERING CO., LTD, Nantong, Jiangsu (CN); TIANJIN UNIVERSITY, Tianjin (CN)

(72) Inventors: Junbo Gong, Tianjin (CN); Qinqing Gu, Jiangsu (CN); Kaifei Zhao, Tianjin (CN); Jiangbo Li, Jiangsu (CN); Baohong Hou, Tianjin (CN); Qiuxiang Yin, Tianjin (CN); Jingkang Wang, Tianjin (CN); Yi Sun, Jiangsu (CN); Shichao Du, Tianjin (CN); Xin Pan, Jiangsu (CN); Zhongshi Liu, Jiangsu (CN)

(73) Assignees: Nantong Licheng Biological Engineering Co., Ltd, Nantong (CN); Tianjin University, Tianjin (CN)

( * ) Notice: Subject to any disclaimer, the term of this patent is extended or adjusted under 35 U.S.C. 154(b) by 0 days.

(21) Appl. No.: 16/062,716

(22) PCT Filed: Nov. 11, 2016

(86) PCT No.: PCT/CN2016/105420
§ 371 (c)(1),
(2) Date: Jun. 15, 2018

(87) PCT Pub. No.: WO2018/086053
PCT Pub. Date: May 17, 2018

(65) Prior Publication Data
US 2018/0370901 A1  Dec. 27, 2018

(51) Int. Cl.
*C07C 227/42* (2006.01)
*C07C 229/08* (2006.01)

(52) U.S. Cl.
CPC .......... *C07C 227/42* (2013.01); *C07C 229/08* (2013.01); *C07B 2200/13* (2013.01)

(58) Field of Classification Search
CPC .. C07C 227/42; C07C 229/08; C07B 2200/13
See application file for complete search history.

(56) References Cited

FOREIGN PATENT DOCUMENTS

| CN | 101928736 | * | 12/2010 |
|---|---|---|---|
| CN | 101928736 A | | 12/2010 |
| CN | 102242161 A | | 11/2011 |
| CN | 103509831 A | | 1/2014 |
| CN | 104531795 A | | 4/2015 |

OTHER PUBLICATIONS

Fabbiani et al. (Pharmaceutical hydrates under ambient conditions from high-pressure seeds: a case study of GABA monohydrate, he Royal Society of Chemistry, Chemical Communications, 50, pp. 1817-1819, Published 2014) (Year: 2014).*

* cited by examiner

*Primary Examiner* — Yevgeny Valenrod
*Assistant Examiner* — Blaine G Doletski

(57) ABSTRACT

The present invention discloses a γ-aminobutyric acid hemihydrate crystal, its molecular formula is $C_4H_9NO_2 \cdot 0.5H_2O$. It also discloses a method of preparing a γ-aminobutyric acid hemihydrate crystal, including first adding crude γ-aminobutyric acid to water to prepare a γ-aminobutyric acid suspension at an initial concentration of 1.2-2.0 g/mL; then stirring the suspension at a constant temperature of 5-10° C. for 6-12 hours, followed by filtering and drying to obtain the γ-aminobutyric acid hemihydrate crystal. The γ-aminobutyric acid hemihydrate crystal is stable, does not easily absorb moisture and agglomerate, and is convenient for further processing and use. The crystal has a large main particle size, uniform particle size distribution, high bulk density, good flowability, and a purity of ≥99%. The preparation method of the crystal according to the present invention is simple, easy to operate, highly efficient and low in energy consumption, and is suitable for large-scale industrial production.

15 Claims, 3 Drawing Sheets

GAMMA-AMINOBUTYRIC ACID HEMIHYDRATE CRYSTAL AND PREPARATION METHOD THEREOF

FIELD OF THE INVENTION

The present invention relates to a hemihydrate crystal and preparation method thereof and, in particular, to a γ-aminobutyric acid hemihydrate crystal and preparation method thereof.

BACKGROUND OF THE INVENTION

γ-aminobutyric acid, chemical name 4-aminobutyric acid, is also known as aminobutyric acid or piperidinic acid. Its molecular formula is $C_4H_9NO_2$, and its molecular mass is 103.1. It appears as a white or off-white crystalline powder; it is a hydrophilic amino acid and is very soluble in water. Its structural formula is as follows:

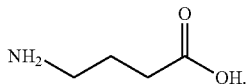

γ-Aminobutyric acid is a naturally occurring, non-proteinogenic amino acid that is widely distributed in prokaryotic and eukaryotic organisms. In mammals, γ-aminobutyric acid is an inhibitory neurotransmitter that mediates more than 40% of inhibitory nerve signals. It has important physiological functions and broad application prospects in medicine and food industry.

In medical research and applications, γ-aminobutyric acid has efficacies in, such as, blood pressure-lowering, anticonvulsant, seizure prevention, sleep quality improvement, antidepression, and brain-cell improvement. The latest researches show that γ-aminobutyric acid also has further efficacies in skin-aging prevention, body odor elimination, lipid metabolism improvement, atherosclerosis prevention, and weight loss. In the food industry, γ-aminobutyric acid can be used in the production of food additives, development of functional dairy products and bakery products. It can also be employed in sports food and beverage industry. On Sep. 27, 2009, the Ministry of Health of the People's Republic of China approved γ-aminobutyric acid as a new resource food.

Patents CN101928736A, CN103509831A, CN104531795A proposed the preparation of γ-aminobutyric acid via evaporative concentration and solventing-out crystallization with 95% ethanol. Patent CN102242161A proposed the preparation of γ-aminobutyric acid by evaporative concentration and cooling crystallization. These different methods all yield γ-aminobutyric acid anhydrate as the product. The crystal morphology of the product is needle-shaped or sheet-shaped, its main particle size is small and unevenly distributed, its bulk density is low and its flowability is low. In addition, anhydrous γ-aminobutyl is highly hygroscopic; when exposed to air, it easily absorbs water and agglomerates into clumps, which is not suitable for further processing and use.

Therefore, it is necessary to provide a γ-aminobutyric acid hemihydrate crystal which is stable, does not easily absorb moisture and agglomerate, has a large main particle size, uniform particle size distribution, high bulk density and good flowability, and a preparation method thereof.

SUMMARY OF THE INVENTION

The objective of the present invention is to overcome the shortcomings of the prior art and to provide a γ-aminobutyric acid hemihydrate crystal and preparation method thereof.

The technical solution of the present invention is:

A γ-aminobutyric acid hemihydrate crystal, the molecular formula of the crystal is $C_4H_9NO_2 \cdot 0.5H_2O$, the structural formula of the crystal is as follows:

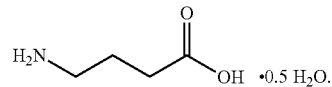

Furthermore, the X-ray powder diffraction pattern of the crystal has characteristic absorption peaks at diffraction angles 2θ of 12.3°±0.2°, 24.5°±0.2°, 26.5°±0.2°, 29.6°±0.2°, 31.6°±0.2°, 36.0°±0.2°, 37.5°±0.2°, and 39 0.5°±0.2°.

Furthermore, the X-ray powder diffraction pattern of the crystal has characteristic absorption peaks at diffraction angles 2θ of 12.3°±0.2°, 17.8°±0.2°, 20.6°±0.2°, 24.5°±0.2°, 25.4°±0.2°, 26.5°±0.2°, 28.5°±0.2°, 29.6°±0.2°, 31.6°±0.2°, 34.6°±0.2°, 36.0°±0.2°, 37.5°±0.2°, 38.4°±0.2°, 39.5°±0.2°.

Furthermore, the crystal exhibits a water loss of 7.9 to 8.1% over 120-180° C. in TGA analysis (Thermogravimetric Analysis); the crystal exhibits an endothermic characteristic peak at (225±2) ° C. in DSC (Differential Scanning calorimetry) analysis.

The present invention also discloses a method of preparing a γ-aminobutyric acid hemihydrate crystal, including the steps of:

S1: Adding crude γ-aminobutyric acid to water to prepare a γ-aminobutyric acid suspension at an initial concentration of 1.2-2.0 g/mL; and S2: Stirring the product of S1 at a constant temperature between 5-10° C. for 6-12 hours, filtering and drying to obtain the γ-aminobutyric acid hemihydrate crystal.

Preferably, step S2 comprises stirring the product of S1 at a constant temperature of 5° C. for 12 hours.

Preferably, step S2 comprises stirring the product of S1 at a constant temperature of 5° C. for 9 hours.

Preferably, the drying in step S2 refers to drying at a temperature between 20-35° C. and a vacuum between 0-0.08 MPa for 8-12 hours.

Preferably, the drying in step S2 refers to drying at a temperature of 35° C. and a vacuum of 0.08 MPa for 12 hours.

Preferably, the drying in step S2 refers to drying at a temperature of 35° C. and at atmospheric pressure for 8 hours.

In the present invention, γ-aminobutyric acid hemihydrate is produced as a result of the oxygen atom of a carboxyl group forming hydrogen bond interactions with a water molecule, so that two γ-aminobutyric acid molecules are linked to one water molecule. In the present invention, a solvate is prepared by suspension crystallization, which is a solvent-mediated polymorphic transformation process; it is divided into three steps: the dissolution of a metastable polymorph, the nucleation of a stable polymorph, and the growth of a stable polymorph. Base on thermodynamic property studies of γ-aminobutyric acid, it was found in an aqueous solution of a certain concentration and temperature, the solubility of the raw material, γ-aminobutyric acid anhydride, is high, and it is a metastable polymorph. On the contrary, the solubility of the product, γ-aminobutyric acid hemihydrate, is low, and it is a stable polymorph. From a thermodynamic point of view, the process of polymorphic transformation in suspension is the gradual dissolution of the metastable γ-aminobutyric acid anhydrate, followed by crystallization to form the stable γ-aminobutyric acid hemihydrate.

Comparing with the prior art, the beneficial effects of the present invention are as follows:

(1) The γ-aminobutyric acid hemihydrate crystal of the present invention is stable, does not easily absorb moisture and agglomerate, and is convenient for further processing and use.

(2) The γ-aminobutyric acid hemihydrate crystal of the present invention has a large main particle size, uniform particle size distribution, high bulk density and good flowability.

(3) The purity of the γ-aminobutyric acid hemihydrate crystal prepared according to the method of the present invention is ≥99%.

(4) The preparation method of γ-aminobutyric acid hemihydrate crystal according to the present invention is simple, easy to operate, highly efficient and low in energy consumption, and is suitable for large-scale industrial production.

BRIEF DESCRIPTION OF THE DRAWINGS

To more clearly illustrate the technical solutions of the present invention, the accompanying drawings mentioned in the embodiments or prior art will be briefly described. It is obvious that the drawings described hereafter are merely embodiments of the present invention. For a person of ordinary skill in the art, other drawings may also be obtained based on these drawings without any creative effort.

DETAILED DESCRIPTION OF THE ILLUSTRATED EMBODIMENTS

The technical solutions in the embodiments of the present invention will be described clearly and completely hereafter with reference to the accompanying drawings. The described embodiments are merely some but not all of the embodiments of the present invention. All other embodiments obtained by a person having ordinary skill in the art based on the embodiments of the present invention without creative efforts shall fall within the protection scope of the present invention.

In the embodiments of the present invention, X-ray diffraction data were obtained using an X-ray powder diffractometer from Rigaku Cooperation (Japan), with a 1050/70 type goniometer, $Cu_{K\alpha}$ radiation, $\lambda=1.54059$ Å, and a scanning speed of 2 degrees/minute. The sample was slightly grounded and smeared on a horizontal background quartz plate to obtain a thin layer.

The particle size distribution curves of the products in the embodiments of the present invention were all determined by Masterizer laser particle size analyzer from Malvern Panalytical (the U.K.).

Embodiment 1

The present invention discloses a method of preparing γ-aminobutyric acid hemihydrate crystals, including the steps of:

S1: 120 g crude γ-aminobutyric acid was added to 100 mL water to prepare a γ-aminobutyric acid suspension;

S2: The product of S1 was stirred at a constant temperature of 5° C. for 9 hours, then filtered to obtain a filter cake. The filter cake was dried at 35° C. and atmospheric pressure for 8 hours until its weight was constant. γ-aminobutyric acid hemihydrate crystals were obtained as the product. The purity of the product was 99.2% as determined by high-performance liquid chromatography (HPLC).

Figure 1:
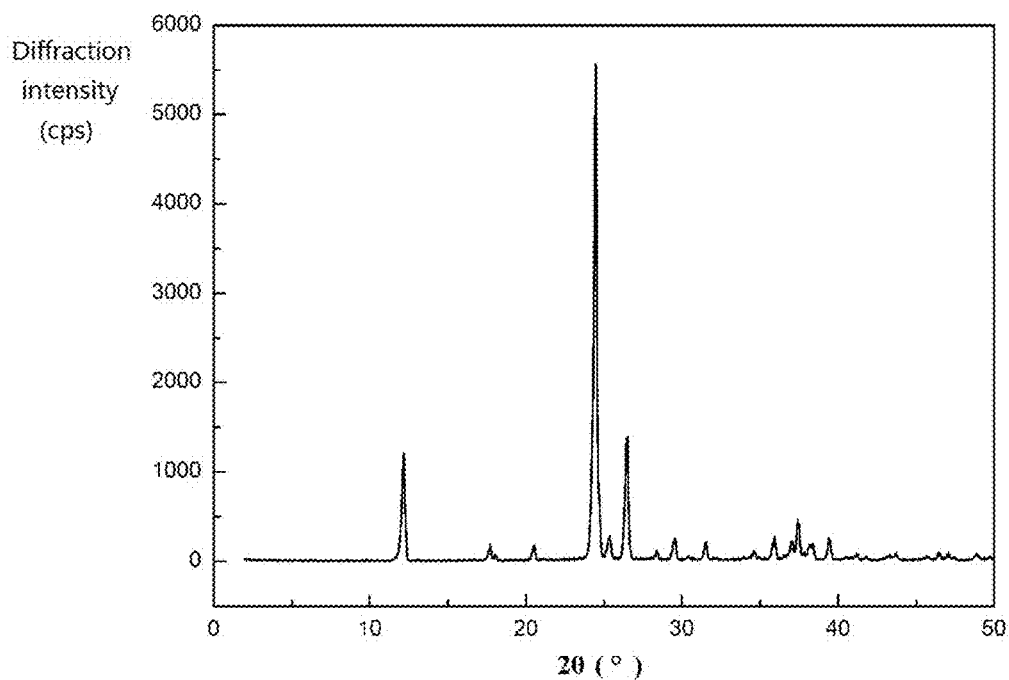
FIG. 1 is an X-ray powder diffraction pattern of γ-aminobutyric acid hemihydrate crystals obtained in embodiment 1 of the present invention.

As shown in FIG. 1, the X-ray powder diffraction pattern of the product had characteristic absorption peaks at diffraction angles 2θ of 12.3°, 17.7°, 20.6°, 24.5°, 25.5°, 26.4°, 28.6°, 29.7°, 31.7°, 34.6°, 36.0°, 37.3°, 38.4° and 39.5°.

Figure 2:
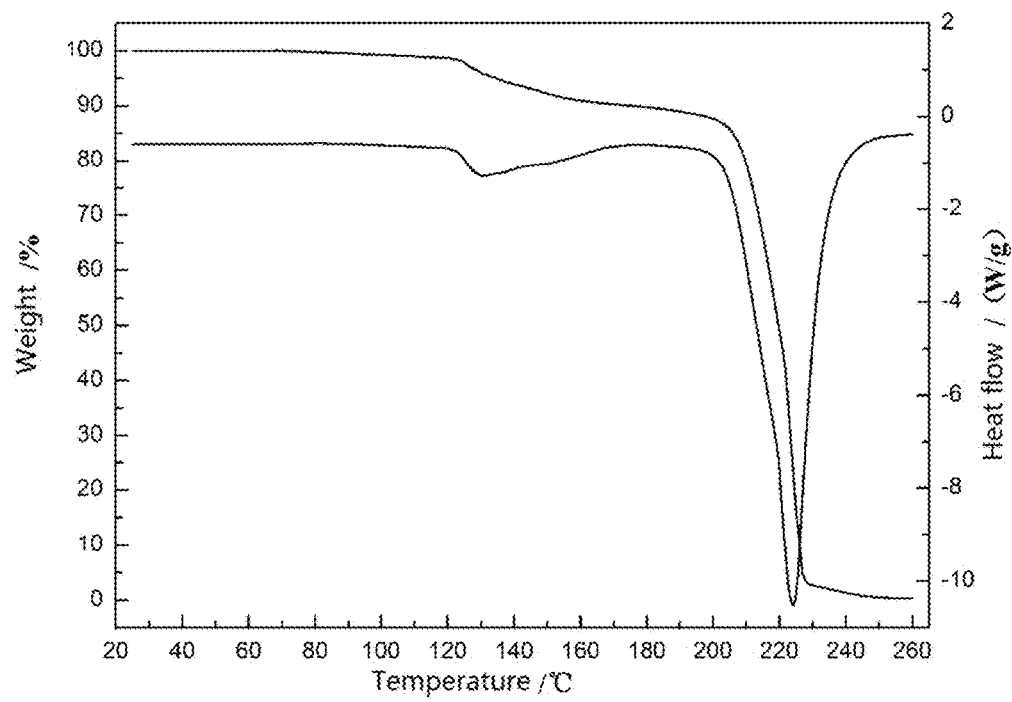
FIG. 2 is a TGA-DSC diagram of γ-aminobutyric acid hemihydrate crystals obtained in embodiment 1 of the present invention.

As shown in FIG. 2, in TGA analysis, the product exhibited a water loss of 7.94% over 120-180° C. In DSC analysis, the product exhibited an endothermic characteristic peak at 225° C.

Figure 3:
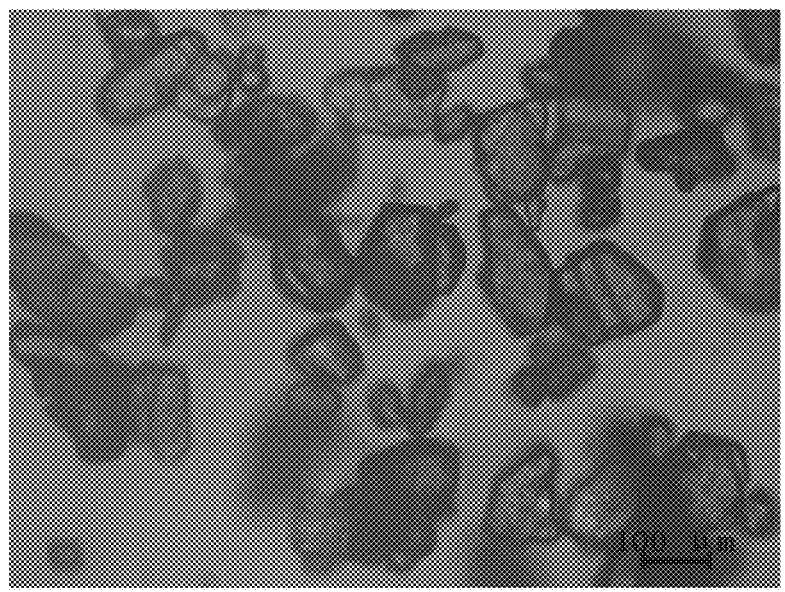
FIG. 3 is an SEM image of γ-aminobutyric acid hemihydrate crystals obtained in embodiment 1 of the present invention.
Figure 4:
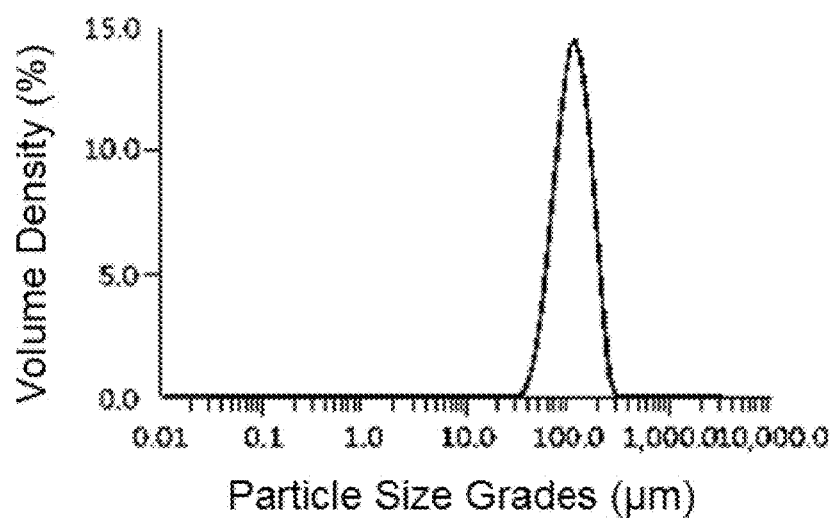
FIG. 4 is a particle size distribution curve of γ-aminobutyric acid hemihydrate crystals obtained in embodiment 1 of the present invention.

As shown in FIG. 3 and FIG. 4, the product was in the form of a block, with a main particle size of 110 μm and a uniform particle size distribution. The product did not easily absorb moisture and agglomerate.

Bulk density test: The bulk density of the crude λ-aminobutyric acid raw material was 0.65 g/mL; the bulk density of the λ-aminobutyric acid hemihydrate crystal product was 0.85 g/mL. This shows that the product had higher bulk density.

Flowability test: The angle of repose is the maximum angle formed between the free slope of a piled powder and the horizontal plane. It is measured when the particles achieve a static state as they slide on the free slope of the piled powder and experience a balance of gravity and interparticle friction. It is the easiest way to examine the flowability of a powder. The smaller the angle of repose, the smaller the friction and the better the flowability. The angle of repose of the crude λ-aminobutyric acid raw material was 50°, and the angle of repose of the λ-aminobutyric acid hemihydrate crystal product was 38°, indicating that the product had good flowability.

Figure 5:
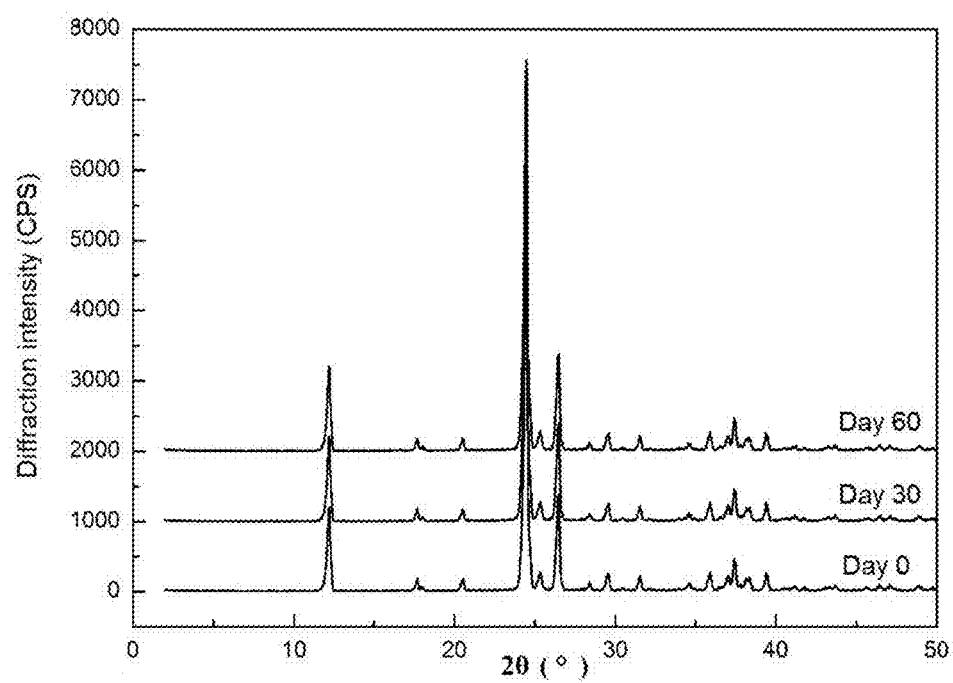
FIG. 5 is a comparative diagram showing X-ray powder diffraction patterns of γ-aminobutyric acid hemihydrate crystals obtained in embodiment 1 of the present invention, after being placed at 30° C. for 60 days.

As shown in FIG. 5, the γ-aminobutyric acid hemihydrate crystal product was placed in a petri dish in a constant temperature and humidity chamber at 30° C. for 60 days. Samples were taken at the 30th and 60th days to measure their X-ray powder diffraction patterns. The results showed that the X-ray powder diffraction patterns did not change significantly. The crystals remained as a white powder, indicating that the stability of the γ-aminobutyric acid hemihydrate crystals was good.

Embodiment 2

The present invention discloses a method of preparing γ-aminobutyric acid hemihydrate crystals, including the steps of:

S1: 200 g crude γ-aminobutyric acid was added to 100 mL water to prepare a γ-aminobutyric acid suspension;

S2: The product of S1 was stirred at a constant temperature of 5° C. for 12 hours, then filtered to obtain a filter cake. The filter cake was dried at 35° C. and 0.08 MPa for 12 hours until its weight was constant. γ-aminobutyric acid hemihydrate crystals were obtained as the product. The purity of the product was 99.6% as determined by high-performance liquid chromatography (HPLC).

The X-ray powder diffraction pattern of the product had characteristic absorption peaks at diffraction angles 2θ of 12.3°, 17.8°, 20.6°, 24.5°, 25.4°, 26.5°, 28.5°, 29.6°, 31.6°, 34.6°, 36.0°, 37.3°, 38.4° and 39.5°.

In TGA analysis, the product exhibited a water loss of 8.06% over 120-180° C. In DSC analysis, the product exhibited an endothermic characteristic peak at 223° C.

The product was in the form of a block, with a main particle size of 100 jam and uniform particle size distribution. The product did not easily absorb moisture and agglomerate. The product had high bulk density and good flowability.

The γ-aminobutyric acid hemihydrate crystal product was placed in a petri dish in a constant temperature and humidity chamber at 30° C. for 60 days. Samples were taken at the 30th and 60th days to measure their X-ray powder diffraction patterns. The results showed that the X-ray powder diffraction patterns did not change significantly. The crystals remained as a white powder, indicating that the stability of the γ-aminobutyric acid hemihydrate crystals was good.

Embodiment 3

The present invention discloses a method of preparing γ-aminobutyric acid hemihydrate crystals, including the steps of:

S1: 135 g crude γ-aminobutyric acid was added to 100 mL water to prepare a γ-aminobutyric acid suspension;

S2: The product of S1 was stirred at a constant temperature of 6° C. for 8 hours, then filtered to obtain a filter cake. The filter cake was dried at 25° C. and 0.05 MPa for 11 hours until its weight was constant. γ-aminobutyric acid hemihydrate crystals were obtained as the product. The purity of the product was 99.1% as determined by high-performance liquid chromatography (HPLC).

The X-ray powder diffraction pattern of the product had characteristic absorption peaks at diffraction angles 2θ of 12.1°, 17.6°, 20.4°, 24.4°, 25.3°, 26.4°, 28.3°, 29.5°, 31.5°, 34.6°, 35.9°, 37.3°, 38.4° and 39.4°.

In TGA analysis, the product exhibited a water loss of 8.02% over 120-180° C. In DSC analysis, the product exhibited an endothermic characteristic peak at 225° C.

The product was in the form of a block, with a main particle size of 120 jam and uniform particle size distribution. The product did not easily absorb moisture and agglomerate. The product had high bulk density and good flowability.

The γ-aminobutyric acid hemihydrate crystal product was placed in a petri dish in a constant temperature and humidity chamber at 30° C. for 60 days. Samples were taken at the 30th and 60th days to measure their X-ray powder diffraction patterns. The results showed that the X-ray powder diffraction patterns did not change significantly. The crystals remained as a white powder, indicating that the stability of the γ-aminobutyric acid hemihydrate crystals was good.

Embodiment 4

The present invention discloses a method of preparing γ-aminobutyric acid hemihydrate crystals, including the steps of:

S1: 200 g crude γ-aminobutyric acid was added to 100 mL water to prepare a γ-aminobutyric acid suspension;

S2: The product of S1 was stirred at a constant temperature of 10° C. for 10 hours, then filtered to obtain a filter cake. The filter cake was dried at 30° C. and 0.07 MPa for 12 hours until its weight was constant. γ-aminobutyric acid hemihydrate crystals were obtained as the product. The purity of the product was 99.5% as determined by high-performance liquid chromatography (HPLC).

The X-ray powder diffraction pattern of the product had characteristic absorption peaks at diffraction angles 2θ of 12.1°, 17.6°, 20.4°, 24.4°, 25.3°, 26.4°, 28.4°, 29.4°, 31.4°, 34.5°, 35.8°, 37.3°, 38.3° and 39.3°.

In TGA analysis, the product exhibited a water loss of 8.10% over 120-180° C. In DSC analysis, the product exhibited an endothermic characteristic peak at 224° C.

The product was in the form of a block, with a main particle size of 96 jam and uniform particle size distribution. The product did not easily absorb moisture and agglomerate. The product had high bulk density and good flowability.

The γ-aminobutyric acid hemihydrate crystal product was placed in a petri dish in a constant temperature and humidity chamber at 30° C. for 60 days. Samples were taken at the 30th and 60th days to measure their X-ray powder diffraction patterns. The results showed that the X-ray powder diffraction patterns did not change significantly. The crystals remained as a white powder, indicating that the stability of the γ-aminobutyric acid hemihydrate crystals was good.

Embodiment 5

The present invention discloses a method of preparing γ-aminobutyric acid hemihydrate crystals, including the steps of:

S1: 150 g crude γ-aminobutyric acid was added to 100 mL water to prepare a γ-aminobutyric acid suspension;

S2: The product of S1 was stirred at a constant temperature of 8° C. for 8 hours, then filtered to obtain a filter cake. The filter cake was dried at 35° C. and atmospheric pressure for 8 hours until its weight was constant. γ-aminobutyric acid hemihydrate crystals were obtained as the product. The purity of the product was 99.4% as determined by high-performance liquid chromatography (HPLC).

The X-ray powder diffraction pattern of the product had characteristic absorption peaks at diffraction angles 2θ of 12.2°, 17.7°, 20.5°, 24.4°, 25.3°, 26.5°, 28.4°, 29.5°, 31.6°, 34.7°, 35.9°, 37.4°, 38.4° and 39.3°.

In TGA analysis, the product exhibited a water loss of 8.00% over 120-180° C. In DSC analysis, the product exhibited an endothermic characteristic peak at 227° C.

The product was in the form of a block, with a main particle size of 106 jam and uniform particle size distribution. The product did not easily absorb moisture and agglomerate. The product had high bulk density and good flowability.

The γ-aminobutyric acid hemihydrate crystal product was placed in a petri dish in a constant temperature and humidity chamber at 30° C. for 60 days. Samples were taken at the 30th and 60th days to measure their X-ray powder diffraction patterns. The results showed that the X-ray powder diffraction patterns did not change significantly. The crystals remained as a white powder, indicating that the stability of the γ-aminobutyric acid hemihydrate crystals was good.

Embodiment 6

The present invention discloses a method of preparing γ-aminobutyric acid hemihydrate crystals, including the steps of:

S1: 120 g crude γ-aminobutyric acid was added to 100 mL water to prepare a γ-aminobutyric acid suspension;

S2: The product of S1 was stirred at a constant temperature of 10° C. for 6 hours, then filtered to obtain a filter cake. The filter cake was dried at 20° C. and 0.05 MPa for 9 hours until its weight was constant. γ-aminobutyric acid hemihydrate crystals were obtained as the product. The purity of the product was 99.2% as determined by high-performance liquid chromatography (HPLC).

The X-ray powder diffraction pattern of the product had characteristic absorption peaks at diffraction angles 2θ of 12.2°, 17.7°, 20.5°, 24.5°, 25.3°, 26.5°, 28.4°, 29.6°, 31.5°, 34.6°, 35.9°, 37.4°, 38.4° and 39.4°.

In TGA analysis, the product exhibited a water loss of 7.90% over 120-180° C. In DSC analysis, the product exhibited an endothermic characteristic peak at 226° C.

The product was in the form of a block, with a main particle size of 90 jam and uniform particle size distribution. The product did not easily absorb moisture and agglomerate. The product had high bulk density and good flowability.

The γ-aminobutyric acid hemihydrate crystal product was placed in a petri dish in a constant temperature and humidity chamber at 30° C. for 60 days. Samples were taken at the 30th and 60th days to measure their X-ray powder diffraction patterns. The results showed that the X-ray powder diffraction patterns did not change significantly. The crystals remained as a white powder, indicating that the stability of the γ-aminobutyric acid hemihydrate crystals was good.

In the present invention, γ-aminobutyric acid hemihydrate is produced as a result of the oxygen atom of a carboxyl group forming hydrogen bond interactions with a water molecule, so that two γ-aminobutyric acid molecules are linked to one water molecule. In the present invention, a solvate is prepared by suspension crystallization, which is a solvent-mediated polymorphic transformation process; it is divided into three steps: the dissolution of a metastable polymorph, the nucleation of a stable polymorph, and the growth of a stable polymorph. Base on thermodynamic property studies of γ-aminobutyric acid, it was found in an aqueous solution of certain concentration and temperature, the solubility of the raw material, γ-aminobutyric acid anhydride, is high, and it is a metastable polymorph. On the contrary, the solubility of the product, γ-aminobutyric acid hemihydrate, is low, and it is a stable polymorph. From a thermodynamic point of view, the process of polymorphic transformation is the gradual dissolution of the metastable γ-aminobutyric acid anhydrate, followed by crystallization to form the stable γ-aminobutyric acid hemihydrate.

Comparing with the prior art, the beneficial effects of the present invention are as follows:

(1) The γ-aminobutyric acid hemihydrate crystal of the present invention is stable, does not easily absorb moisture and agglomerate, and is convenient for further processing and use.

(2) The γ-aminobutyric acid hemihydrate crystal of the present invention has a large main particle size, uniform particle size distribution, high bulk density and good flowability.

(3) The purity of the γ-aminobutyric acid hemihydrate crystal prepared according to the method of the present invention is ≥99%.

(4) The preparation method of γ-aminobutyric acid hemihydrate crystal according to the present invention is simple, easy to operate, highly efficient and low in energy consumption, and is suitable for large-scale industrial production.

The description above illustrates the preferred embodiments of the present invention. It should be pointed out that for those skilled in the art, a number of improvements can be made without departing from the principle of the present invention. These improvements are also considered as within the scope of protection of the present invention.

What is claimed is:

1. A γ-aminobutyric acid hemihydrate crystal, wherein the molecular formula of the crystal is $(C_4H_9NO_2)_2 \cdot H_2O$, the structural formula of the crystal is as follows:

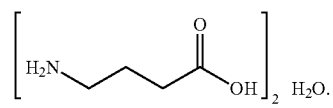

2. The γ-aminobutyric acid hemihydrate crystal according to claim 1, wherein the X-ray powder diffraction pattern of the crystal has characteristic absorption peaks at diffraction angles 2θ of 12.3°±0.2°, 24.5°±0.2°, 26.5°±0.2°, 29.6θ±0.2°, 31.6°±0.2°, 36.0°±0.2°, 37.5°±0.2°, and 39.5°±0.2°.

3. The γ-aminobutyric acid hemihydrate crystal according to claim 1, wherein the X-ray powder diffraction pattern of the crystal has characteristic absorption peaks at diffraction angles 2θ of 12.3°±0.2°, 17.8°±0.2°, 20.6°±0.2°, 24.5°±0.2°, 25.4°±0.2°, 26.5°±0.2°, 28.5°±0.2°, 29.6°±0.2°, 31.6°±0.2°, 34.6°±0.2°, 36.0°±0.2°, 37.5°±0.2°, 38.4°±0.2°, 39.5°±0.2°.

4. The γ-aminobutyric acid hemihydrate crystal according to claim 3, wherein the crystal exhibits a water loss of 7.9% to 8.1% over 120-180'C in TGA analysis; the crystal exhibits an endothermic characteristic peak at (225±2) ° C. in DSC analysis.

5. A method of preparing the γ-aminobutyric acid hemihydrate crystal according to claim 1, comprising the steps of:
S1: adding crude γ-aminobutyric acid to water to prepare a γ-aminobutyric acid suspension at an initial concentration of 1.2 g/mL to 2.0 g/mL; and
S2: stirring the product of S1 at a constant temperature between 5-10° C. for 6-12 hours, filtering and drying to obtain the γ-aminobutyric acid hemihydrate crystal.

6. The method of preparing the γ-aminobutyric acid hemihydrate crystal according to claim 5, wherein step S2 comprises stirring the product of S1 at a constant temperature of 5° C. for 12 hours.

7. The method of preparing the γ-aminobutyric acid hemihydrate crystal according to claim 5, wherein step S2 comprises stirring the product of S1 at a constant temperature of 5° C. for 9 hours.

8. The method of preparing the γ-aminobutyric acid hemihydrate crystal according to claim 6, wherein the drying in step S2 is drying at a temperature between 20-35° C. and a vacuum between 0-0.08 MPa for 8-12 hours.

9. The method of preparing the γ-aminobutyric acid hemihydrate crystal according to claim 8, wherein the drying in step S2 is drying at a temperature of 35° C. and a vacuum of 0.08 MPa for 12 hours.

10. The method of preparing the γ-aminobutyric acid hemihydrate crystal according to claim 8, wherein the drying in step S2 is drying at a temperature of 35° C. and at atmospheric pressure for 8 hours.

11. The γ-aminobutyric acid hemihydrate crystal according to claim 2, wherein the X-ray powder diffraction pattern of the crystal has characteristic absorption peaks at diffraction angles 2θ of 12.3°±0.2°, 17.80±0.2°, 20.6°±0.2°, 24.5°±0.2°, 25.4°±0.2°, 26.5°±0.2°, 28.5°±0.2°, 29.6°±0.2°, 31.6°±0.2°, 34.6°±0.2°, 36.0°±0.2°, 37.5°±0.2°, 38.4°±0.2°, 39.5°±0.2°.

12. The γ-aminobutyric acid hemihydrate crystal according to claim 11, wherein the crystal exhibits a water loss of 7.9% to 8.1% over 120-180° C. in TGA analysis; the crystal exhibits an endothermic characteristic peak at (225±2) ° C. in DSC analysis.

13. The method of preparing the γ-aminobutyric acid hemihydrate crystal according to claim 7, wherein the drying in step S2 is drying at a temperature between 20-35° C. and a vacuum between 0-0.08 MPa for 8-12 hours.

14. The method of preparing the γ-aminobutyric acid hemihydrate crystal according to claim 13, wherein the drying in step S2 is drying at a temperature of 35° C. and a vacuum of 0.08 MPa for 12 hours.

15. The method of preparing the γ-aminobutyric acid hemihydrate crystal according to claim 13, wherein the drying in step S2 is drying at a temperature of 35° C. and at atmospheric pressure for 8 hours.

\* \* \* \* \*